United States Patent [19]

Wickenhaeuser et al.

[11] Patent Number: 4,521,632

[45] Date of Patent: Jun. 4, 1985

[54] PURIFICATION OF AQUEOUS GLYOXAL SOLUTIONS

[75] Inventors: Gerhard Wickenhaeuser, Birkenheide; Bernd Heida, Boehl-Iggelheim; Fritz Graf, Speyer; Leopold Hupfer, Friedelsheim, all of Fed. Rep. of Germany

[73] Assignee: BASF Aktiengesellschaft, Ludwigshafen, Fed. Rep. of Germany

[21] Appl. No.: 572,948

[22] Filed: Jan. 23, 1984

[30] Foreign Application Priority Data

Jan. 29, 1983 [DE] Fed. Rep. of Germany ....... 3303010

[51] Int. Cl.$^3$ ..................... C07C 45/78; C07C 45/80
[52] U.S. Cl. .................................................. 568/492
[58] Field of Search ......................................... 568/492

[56] References Cited

U.S. PATENT DOCUMENTS 3,270,062  4/1966  Merz et al. .................... 568/492
3,860,156  8/1975  Lawrence .
3,860,656  1/1975  McCain et al. ................ 568/492
4,065,506 12/1977  Wessendorf et al. ........... 568/492

Primary Examiner—Werren B. Lone
Attorney, Agent, or Firm—John H. Shurtleff

[57] ABSTRACT

Aqueous solutions of glyoxal which contain acids are purified by treatment with a solution which contains from 20 to 60% by weight of a tertiary amine and from 80 to 40% by weight of an alcohol which is not infinitely miscible with water, the treatment being carried out by mixing the two solutions during a residence time of less than 5 minutes.

14 Claims, No Drawings

PURIFICATION OF AQUEOUS GLYOXAL SOLUTIONS

Glyoxal is used as, for example, an assistant in the textile and paper making industry and is prepared, as is known, by oxidation of acetaldehyde or by oxidative dehydrogenation of ethylene glycol. These processes give aqueous glyoxal solutions which contain impurities and therefore have to be purified before being used. For example, the crude glyoxal prepared by oxidizing acetaldehyde with nitric acid contains substantial amounts of formic acid and acetic acid, the concentrations of which can be reduced to a few percent by steam distillation, and a small amount of sparingly volatile acids, such as glyoxylic acid, glycolic acid and oxalic acid, which remain in the bottom product, i.e. the crude glyoxal solution.

Although the glyoxal prepared from glycol by the dehydrogenation process contains relatively small amounts of acids, as a rule not more than 2%, it too has to be purified, since, in order to use the glyoxal commercially, the acid number has to be <1. This crude glyoxal also contains the above acids, but in this case the amount of sparingly volatile acids is substantially larger compared with the total acid content. Apart from the acids, the pronounced yellow coloration of the crude glyoxal solutions is also troublesome.

To purify the crude aqueous glyoxal solutions, it has been proposed to remove the acids from these solutions by treatment with a solid ion exchanger. This process, which is disclosed in U.S. Pat. 3,270,062, has the disadvantage that the procedure is carried out batchwise. In addition, the ion exchanger has to be regenerated frequently owing to the high acid number of the crude glyoxal solution. Moreover, substantial amounts of dilute glyoxal solutions are obtained, from which the commercial 40% strength solution can be obtained only with the consumption of a substantial amount of energy.

According to a process described in U.S. Pat. 3,860,656, the acidic impurities are removed from the crude aqueous glyoxal solution by treatment with a solution of a high molecular weight tertiary amine or a quaternary ammonium bicarbonate in an organic solvent. In this process, the two solutions are fed countercurrent to one another in a multi-stage extraction column. Although continuous purification is achieved, residence times of about one hour are required. Moreover, in order to avoid excessively large losses of glyoxal, the organic phase has to be washed with water so that in this process too the energy-consumptive concentration procedure for obtaining commercial glyoxal solutions cannot be dispensed with. According to Ind. Eng. Chem. Process Des. Dev. 19, 1980, 494–497, a very large variety of organic solvents have been tested for the purification of glyoxal solutions, in single-stage extraction experiments. It has been found that the solvents have very different actions and, for example where a mixture of kerosene and isodecanol is used, a glyoxal solution having a high residual acid content is obtained. In this case too, it was found that adequate purification is achieved only in a single-stage extraction with an inevitably long residence time.

We have found that, in the purification of aqueous solutions of glyoxal which contain acids by treatment with a solution of a tertiary amine in an organic solvent, the stated disadvantages are overcome if the treating agent used is a solution which contains from 20 to 60% by weight of a tertiary amine and from 80 to 40% by weight of an alcohol which is not infinitely miscible with water, and the treatment is carried out by mixing the two solutions during a residence time of less than 5 minutes.

The novel process surprisingly gives high purification coupled with very low losses of glyoxal by a single-stage procedure and in extremely short residence times.

Using the novel process, it is possible to purify aqueous glyoxal solutions which are obtained, for example, in the conventional oxidation of acetaldehyde with nitric acid or the dehydrogenation of glycol, and which usually have an acid number of from 5 to 200. Suitable aqueous glyoxal solutions are those of the above type which contain from 20 to 50, in particular from 35 to 45, % by weight of glyoxal.

The purifying agent used is, in accordance with the invention, a solution which contains from 20 to 60, preferably from 30 to 50, % by weight of a tertiary amine and from 80 to 40, preferably from 70 to 50, % by weight of an alcohol which is not infinitely miscible with water. The tertiary amine used is advantageously a straight-chain or branched aliphatic amine having a molecular weight of from 300 to 600, for example trioctylamine, trinonylamine, tridecylamine, tridodecylamine and isomers of these amines. It is also possible to use a mixture of different amines of the stated type.

Suitable alcohols which are not infinitely miscible with water are straight-chain or branched primary, secondary or tertiary alkanols of more than 3 carbon atoms, aliphatic alcohols of 4 to 15, preferably 8 to 13 carbon atoms being particularly suitable. Examples of such alcohols include pentanol, hexanol, 2-ethylhexanol, octanol, decanol and isodecanol.

In the novel process, the aqueous glyoxal solution and the alcoholic solution of the tertiary amine are mixed at as high as 60° C., advantageously at room temperature. The two phases are preferably mixed in a single stage by passing them simultaneously into a mixing vessel, the residence time being less than 5 minutes. Particularly useful for this purpose are mixing vessels which permit a rapid throughput and thorough mixing. The ratio of the volume of the glyoxal solution to that of the amine solution is advantageously kept at from 1:0.2 to 1:3, and the residence time is preferably from 0.1 to 2 minutes.

After the mixing procedure, the two solutions are separated from one another by phase separation. This results directly in an aqueous glyoxal solution having an acid number of less than 1. In the process according to the invention, glyoxal losses of less than 1% can be achieved. This is very surprising since the method for avoiding glyoxal losses which is described in U.S. Pat. 3,860,656 recommends washing the organic phase with water. Surprisingly, we have also found that, in the novel process, the major part of the color-imparting component of the crude glyoxal solution is extracted. Hence, a purified aqueous glyoxal solution which can be used directly for many purposes is obtained. If desired, the purity of the aqueous glyoxal solution can be improved, for example by subsequent treatment with active carbon. This gives a glyoxal solution having a color number of about 10 APHA and containing a few ppm of solvent.

The solvent phase is regenerated in a conventional manner by treatment with an alkaline agent, e.g. sodium hydroxide, potassium hydroxide or sodium bicarbonate.

EXAMPLE 1

10 kg/hour of an aqueous 40% strength glyoxal solution having an acid number of 14.2 and a color number of 170 APHA and 4 kg/hour of a 40% strength solution of tridodecylamine in 2-ethylhexanol are passed simultaneously into a stirred vessel having a capacity of 70 ml. The glyoxal solution is obtained by oxidative dehydrogenation of ethylene glycol. The residence time in this mixing process is 20 seconds. The treated mixture passes from the stirred vessel directly into a phase separator, in which the aqueous phase is separated off from the organic phase. The aqueous glyoxal solution purified in this manner has an acid number of 0.6 and a color number of 30 APHA. The organic phase contains 0.6% of glyoxal, corresponding to a glyoxal loss of 0.6%.

EXAMPLE 2

The procedure described in Example 1 is followed, except that 4 kg/hour of a 40% strength solution of tridodecylamine in isodecanol is used instead of the solution of tridodecylamine in 2-ethylhexanol. The purified aqueous glyoxal solution has an acid number of 0.45. The organic phase contains 0.55% of glyoxal, corresponding to a glyoxal loss of 0.55%. The aqueous glyoxal solution is treated by suspending 0.3% of an active carbon in it, after which it has a color number of 9 APHA and contains 2 ppm of solvent.

EXAMPLE 3

6 kg/hour of an aqueous 42% strength glyoxal solution having a total acid number of 74 and 12 kg/hour of a mixture of 40% by weight of tridodecylamine and 60% by weight of isodecanol are passed simultaneously into a stirred vessel having a capacity of 70 ml. The glyoxal solution is obtained by oxidizing acetaldehyde with nitric acid. The residence time in the mixing process is 14 seconds, and the phases are separated as described in Example 1. The glyoxal solution has an acid number of 1.07, and the glyoxal loss is 0.6%.

EXAMPLE 4

0.47 kg/hour of an aqueous 40% strength glyoxal solution having an acid number of 12.5 and 0.23 kg/hour of a 40% strength solution of tridodecylamine in 2-ethylhexanol are passed simultaneously into a stirred vessel having a capacity of 30 cm$^3$. The glyoxal solution is obtained by oxidative dehydrogenation of ethylene glycol. The residence time in the mixing process is 3.2 minutes. The mixture passes from the stirred vessel directly into a phase separator. After the two phases have been separated, the resulting glyoxal solution has an acid number of 0.56. The organic phase contains 2.1% of glyoxal, corresponding to a glyoxal loss of 2.5%.

EXAMPLE 5

The procedure described in Example 4 is followed, except that 1.9 kg/hour of an aqueous 40% strength crude glyoxal solution and 0.8 kg/hour of a 40% strength solution of trioctylamine in 2-ethylhexanol are passed into a stirred vessel. The residence time in the stirring process is 0.83 minute. The resulting glyoxal solution has an acid number of 0.86, and the organic phase contains 1.3% of glyoxal.

EXAMPLE 6

10.2 kg/hour of an aqueous 40% strength glyoxal solution having an acid number of 15.3 and 4.5 kg/hour of a solution of 40% by weight of trioctylamine and 60% by weight of isodecanol are passed simultaneously into a stirred vessel having a capacity of 70 ml. The glyoxal solution is obtained by oxidative dehydrogenation of ethylene glycol. The residence time in the mixing process is 19 seconds. The treated mixture passes from the mixing vessel directly into a phase separator. The glyoxal solution purified in this manner has an acid number of 0.85. The organic phase contains 0.25% of glyoxal, corresponding to a glyoxal loss of 0.27%.

EXAMPLE 7 (comparative experiment)

Use of a solution of a tertiary amine in (a) butyl acetate or (b) methyl isobutyl ketone as an organic solvent:
(a) 5 kg/hour of an aqueous 40% strength glyoxal solution having an acid number of 12.5 and 2.4 kg/hour of a 40% strength solution of tridodecylamine in butyl acetate are passed simultaneously into a stirred vessel having a capacity of 30 ml. The glyoxal solution is obtained by oxidative dehydrogenation of ethylene glycol. The residence time in the mixing process is 16 seconds. The treated mixture passes from the stirred vessel directly into a phase separator. After the two phases have been separated, the resulting glyoxal solution has an acid number of 3.4. The organic phase contains 0.59% of glyoxal, corresponding to a loss of 0.71%.
(b) The procedure described above is followed, except that methyl isobutyl ketone is used as a solvent for the tridodecylamine. The resulting glyoxal solution has an acid number of 2.4. The organic phase contains 0.6% of glyoxal, corresponding to a loss of 0.75%.

EXAMPLE 8 (comparative experiment)

Extraction in an extraction column for relatively long residence times, as described in U.S. Patent 3,860,656.

1.75 kg/hour of a 40% strength aqueous glyoxal solution, obtained by oxidation of ethylene glycol and having an acid number of 14.1, are passed into a pulsating packed extraction column having a diameter of 4 cm and a height of 4 m. At the same time, 6 kg/hour of a 20% strength solution of tridodecylamine in toluene, as a disperse phase, are passed countercurrent to the above solution. The mean residence time for the glyoxal solution in this extraction is 2.9 hours. The glyoxal solution run off has an acid number of 1.2. The amine solution contains 0,95% of glyoxal, corresponding to a total glyoxal loss of 8.1%.

We claim:
1. In a process for the purification of an aqueous glyoxal solution which contains acids as impurities by treatment with a solution of a tertiary amine in an organic solvent, the improvement which comprises:
preparing as the treating agent a solution which contains from 20 to 60% by weight of a tertiary amine and from 80 to 40% by weight of an alcohol which is not infinitely miscible with water; and
carrying out the treatment by mixing the two solutions at a temperature of from about room temperature up to 60° C. and during a residence time of less than 5 minutes.
2. A process as claimed in claim 1, wherein the two solutions are mixed in a single stage in a mixing vessel.

3. A process as claimed in claim 1, wherein the residence time is from 0.1 to 2 minutes.

4. A process as claimed in claim 1, wherein the volume ratio of the glyoxal solution to the amine solution is from 1:0.2 to 1:3.

5. A process as claimed in claim 1 wherein the alcohol of the treating agent is selected from the group consisting of straight-chain or branched primary, secondary or tertiary alkanols of more than 3 carbon atoms.

6. A process as claimed in claim 1 wherein the alcohol of the treating agent is an aliphatic alcohol of 4 to 15 carbon atoms.

7. A process as claimed in claim 1 wherein the alcohol of the treating agent is an aliphatic alcohol of 8 to 13 carbon atoms.

8. A process as claimed in claim 1 wherein the alcohol of the treating agent is selected from the group consisting of pentanol, hexanol, 2-ethylhexanol, octanol, decanol and isodecanol.

9. A process as claimed in claim 8 wherein the alcohol is 2-ethylhexanol.

10. A process as claimed in claim 8 wherein the alcohol is isodecanol.

11. A process as claimed in claim 8 wherein the volume ratio of the glyoxal solution to the amine solution is from 1:0.2 to 1:3, and the two solutions are mixed in a single stage in a mixing vessel.

12. A process as claimed in claim 11 wherein the residence time of the mixing is from 0.1 to 2 minutes.

13. A process as claimed in claim 12 wherein the alcohol of the treating agent is 2-ethylhexanol.

14. A process as claimed in claim 12 wherein the alcohol of the treating agent is isodecanol.

* * * * *